United States Patent
Shaw

(10) Patent No.: US 10,492,934 B2
(45) Date of Patent: Dec. 3, 2019

(54) MEDICAL DEVICE FIXATION ANCHOR HAVING IMPROVED COMPACTION AND DELIVERY

(71) Applicant: W. L. Gore & Associates, Inc., Newark, DE (US)

(72) Inventor: Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/804,408

(22) Filed: Nov. 6, 2017

(65) Prior Publication Data

US 2018/0110635 A1 Apr. 26, 2018

Related U.S. Application Data

(63) Continuation of application No. 12/817,230, filed on Jun. 17, 2010, now Pat. No. 9,808,361.

(60) Provisional application No. 61/187,688, filed on Jun. 17, 2009.

(51) Int. Cl.
*A61F 2/82* (2013.01)
*A61F 2/86* (2013.01)
*A61F 2/848* (2013.01)

(52) U.S. Cl.
CPC ........ *A61F 2/86* (2013.01); *A61F 2002/8483* (2013.01); *A61F 2220/0016* (2013.01)

(58) Field of Classification Search
CPC ....................................................... A61F 2/82
See application file for complete search history.

(56) References Cited

U.S. PATENT DOCUMENTS

| | | | |
|---|---|---|---|
| 5,423,851 A | 6/1995 | Samuels | |
| 6,007,558 A | 12/1999 | Ravenscroft et al. | |
| 6,042,605 A | 3/2000 | Martin et al. | |
| 6,361,637 B2 | 3/2002 | Martin | |
| 6,517,573 B1 | 2/2003 | Pollock et al. | |
| 6,520,986 B2 | 2/2003 | Martin | |
| 2003/0220683 A1 | 11/2003 | Minasian et al. | |
| 2004/0010312 A1 | 1/2004 | Enayati | |
| 2006/0069406 A1 | 3/2006 | Hendriksen et al. | |
| 2008/0132996 A1 | 6/2008 | Drasler et al. | |
| 2009/0082847 A1 | 3/2009 | Zacharias et al. | |

FOREIGN PATENT DOCUMENTS

| | | |
|---|---|---|
| CN | 1555769 A | 12/2004 |
| CN | 2887334 Y | 4/2007 |
| CN | 101234046 A | 8/2008 |
| CN | 101351168 A | 1/2009 |
| EP | 0701800 A1 | 3/1996 |
| EP | 732088 A2 | 9/1996 |
| EP | 1880693 A1 | 1/2008 |
| JP | 2005525910 A | 9/2005 |
| WO | WO-0176509 A1 | 10/2001 |

(Continued)

OTHER PUBLICATIONS

International Search Report and Written Opinion, PCT/US2010/001748, dated Aug. 4, 2010, 13 pages.

(Continued)

*Primary Examiner* — Matthew W Schall

(57) ABSTRACT

A medical fixation device having a device attachment portion, a compression bearing portion and a barb portion. The barb portion is separated from a device constraining means by the incorporation of the compression bearing portion.

20 Claims, 3 Drawing Sheets

(56) References Cited

FOREIGN PATENT DOCUMENTS

| WO | WO-2003099167 A3 | 12/2003 |
| WO | WO-2005099627 A1 | 10/2005 |
| WO | WO-2005102214 A1 | 11/2005 |

OTHER PUBLICATIONS

International Search Report and Written Opinion, PCT/US2010/001765, dated Oct. 5, 2010, 14 pages.

MEDICAL DEVICE FIXATION ANCHOR HAVING IMPROVED COMPACTION AND DELIVERY

CROSS REFERENCE TO RELATED APPLICATIONS

This application is a continuation of U.S. application Ser. No. 12/817,230, filed Jun. 17, 2010, which claims priority to U.S. Provisional Ser. No. 61/187,688, filed Jun. 17, 2009, both of which are herein incorporated by reference in their entireties.

BACKGROUND OF THE INVENTION

Field of the Invention

The invention relates to a medical device fixation anchor and in particular with an anchor that enhances the methods of compressing the anchor into a constraining means along with the method of releasing the constraining means.

Discussion of the Related Art

Various medical devices require some form of fixation or anchoring to a targeted site. Common anchoring means include barbs, hooks, sutures or other features used to attach a device to the surrounding anatomy. Some examples of devices requiring a means to anchor include vena-cava filters, stents, stent grafts, bile/urinary duct stents, intestinal/gastro stents and liners, occluders, electrophysiological leads, various monitors or diagnostic devices, central venous catheters and other devices as commonly know in the art. Many of these devices are pre-compacted and constrained to a small profile to allow minimally invasive delivery to an anatomical site. Once positioned at the desired site, the constraining means is removed, allowing the device to self expand and engage the surrounding anatomy.

Current anchors often interfere with the device compaction process. For example, as the device is forced into a small diameter constraining means, the sharp tip of a barb can snag or puncture the constraining means. Current anchors can also compromise the removal of a constraining means. For example, as the constraining means is being removed, a sharp anchor barb can penetrate the constraint, resulting in a delivery failure or other complication.

SUMMARY OF THE INVENTION

An embodiment of the present invention includes a medical fixation device, comprising
a flexible anchor having a device attachment portion, a compression bearing portion, and a barb portion;
the device attachment portion being coupled to a medical device;
the compression bearing portion being positioned between the device attachment portion and the barb portion;
the flexible anchor having an expanded state and a compacted state;
the compacted state being maintained by a removable constraint;
while in the compacted state the compression bearing portion being in contact with the removable constraint; and
while in the compacted state the barb portion being separated from the removable constraint.

Additional features and advantages of the invention will be set forth in the description or may be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, to illustrate embodiments of the invention, and together with the description serve to explain the principles of the invention.

DETAILED DESCRIPTION OF THE ILLUSTRATED EMBODIMENTS

The invention is directed to a medical device anchoring or fixation means that enhances the ease of initial compaction and subsequent device deployment.

Figure 1A:
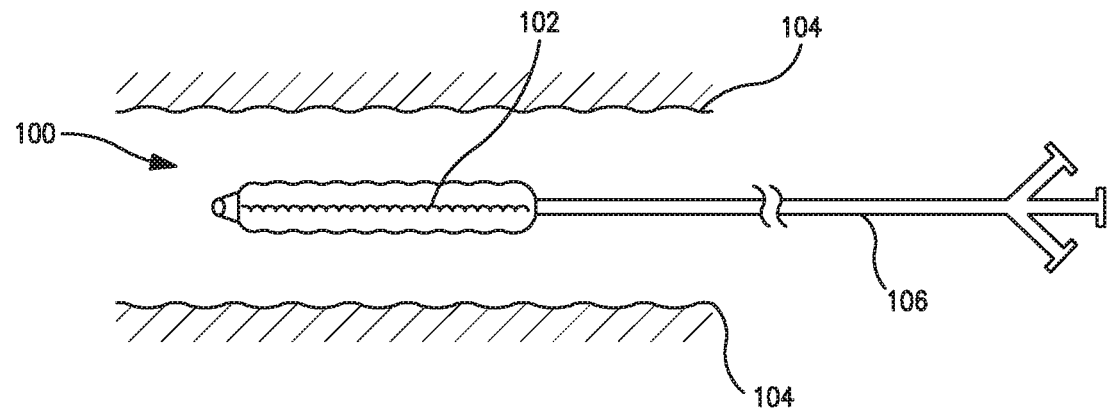
FIG. 1A is a partial side view of a medical device prior to implantation. The medical device is shown in a compacted state, the compacted state is maintained by a constraining means.
Figure 1B:
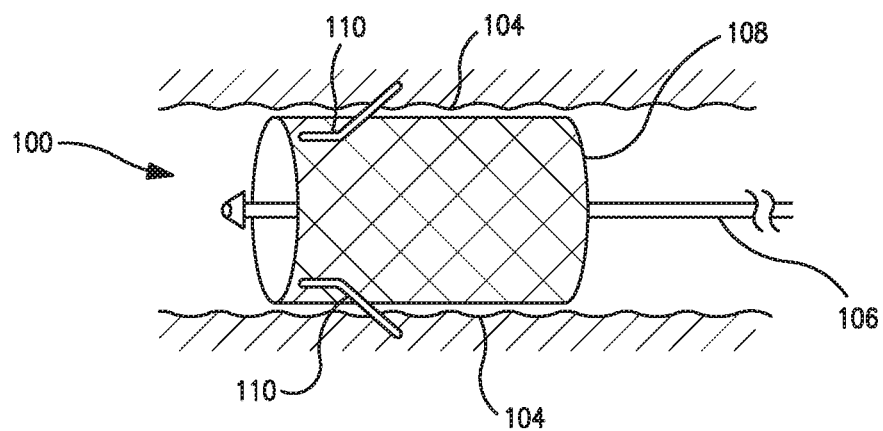
FIG. 1B is a partial side view of medical device that has self-expanded after the removal of the constraining means.

FIGS. 1A and 1B show a general example of a medical device delivery sequence. Shown in partial side view, FIG. 1A is a compacted medical device 100. The specific medical device shown is a self expanding stent graft, having a removable sheath constraining means 102. The medical device is shown positioned within a vessel 104. The constrained medical device is shown compacted onto a delivery catheter 106.

Shown in partial side view, FIG. 1B is the medical device 100 in an expanded state. Shown is a self-expanding stent graft 108, the delivery catheter 106 and two flexible anchors 110. The two flexible anchors 110 are shown at least partially penetrating the vessel 104.

Figure 2A:
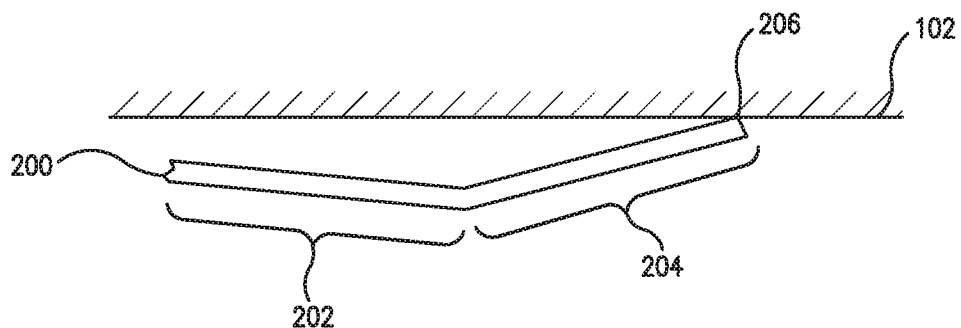
FIGS. 2A and 2B are partial side views of commonly known flexible anchors, shown in compacted and expanded states.
Figure 2B:
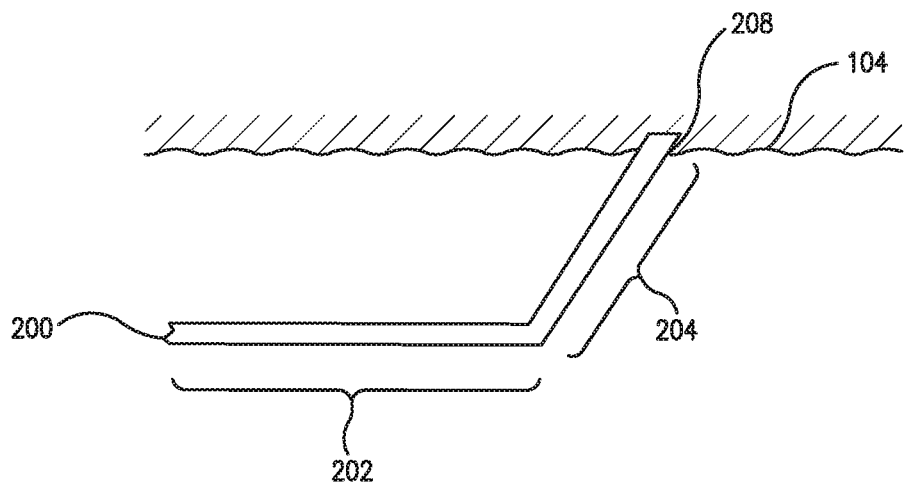

FIGS. 2A and 2B show partial side views of a typical medical device anchor. Shown in FIG. 2A is a flexible anchor 200 in a constrained or compressed state. The anchor 200 has a device attachment portion 202 useful to join the anchor to the medical device, and a barb portion 204. The flexible anchor is shown constrained by a constraining means 102. As shown in FIG. 2A, the anchor barb portion 204 is forced into contact with the constraining means 102, resulting in an interference point 206. The interference at point 206 between the sharp barb and the constraining means can allow the barb to penetrate the constraining means, or create excess friction that could compromise the removal of the constraining means 102.

As shown in FIG. 2B, the device attachment portion 202 and the barb portion 204 of the anchor have self-expanded to engage a lumen wall 104 upon removal of the constraining means. Also shown is an interference or penetration point 208 between the barb and the vessel.

Figure 3A:
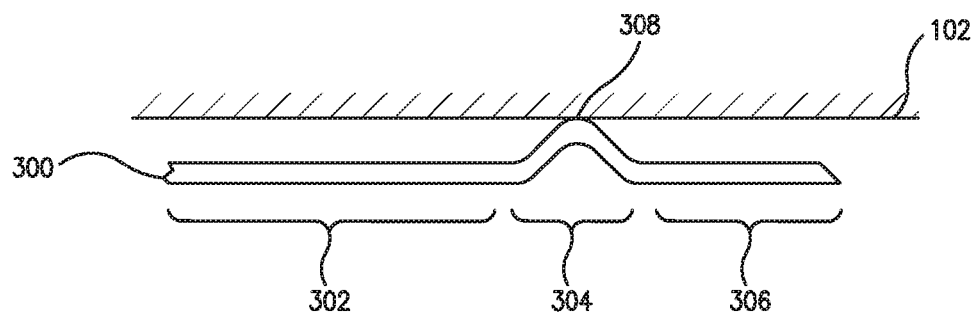
FIGS. 3A and 3B show partial side views of an improved anchor incorporating a compression bearing portion.
Figure 3B:
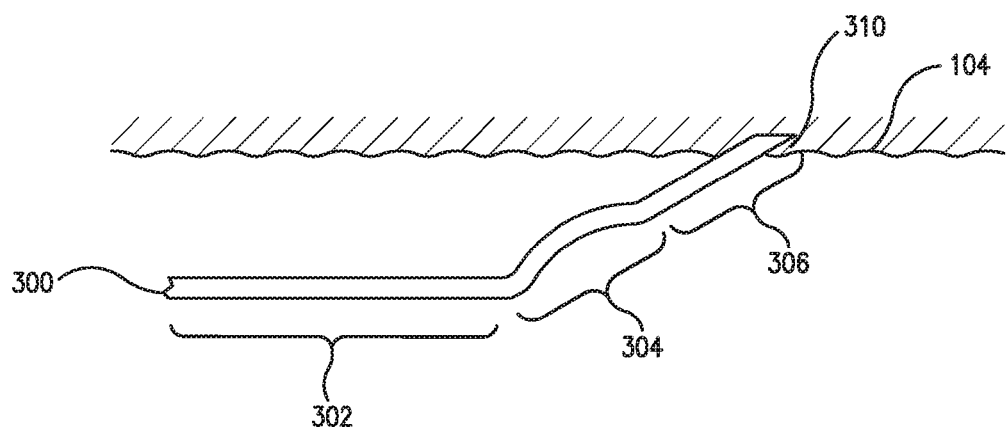

FIGS. 3A and 3B are partial side views of an improved flexible anchor. The anchor 300 has a device attachment portion 302, a compression bearing portion 304 and a barb portion 306. The barb portion may be of any desired length effective to puncture a lumen wall or other desired location for attachment of the anchor device. As shown in FIG. 3A, the flexible anchor 300 is constrained to a compacted shape by a constraining means 102. The constraining means 102 bears against the compression bearing portion 304 at contact point 308. As shown in a compacted state, the barb portion 306 is separated from the constraining means 102. The separation between the barb portion and the constraining means is caused by the shape of the compression bearing portion 304. A compression bearing portion 304 can be configured in a variety of ways and may include curved, protruding, flat or any other profile that will affect a separation between a barb and a constraining means while in a constrained state.

As shown in FIG. 3B, the device attachment portion 302, the compression bearing portion 304 and the barb portion 306 of the anchor 300 have self-expanded to engage the vessel wall 104 upon removal of the constraining means. Also shown is an interference or penetration point 310 between the barb and the vessel.

The medical device shown in FIGS. 1 through 3 is a self expanding stent graft that is held in a constrained state by a constraining sheath 102. The constraining sheath may utilize a pull cord terminating in a "rip-cord" stitch. When tensioned, the pull cord "un-stitches" to release the constraining sheath. Stent grafts and constraining sheaths can be fabricated according to the methods and materials as generally disclosed in, for example, U.S. Pat. No. 6,042,605 issued to Martin et al., U.S. Pat. No. 6,361,637 issued to Martin et al. and U.S. Pat. No. 6,520,986 issued to Martin et al.

A removable constraining means for a self-expanding medical device can include sheaths that are subsequently removed or left adjacent to the implanted device. Multiple sheaths can be used with a single or with multiple devices. Other forms of removable constraints include "pull-back" or "push-out" tubes, frangible constraints, removable constraining stitches or pins or any other suitable means as known in the art.

Depending upon the intended use, flexible anchors can comprise commonly known materials (or combinations of materials) such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), metals, nitinols, Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX), bio-absorbable materials and metals such as stainless steel, nickel/titanium alloys, and the like.

Typical methods used in the assembly of anchors to medical devices include commonly known techniques used to attach two or more components. Examples of permanent attachments include the use of glues, adhesives, welds, insert molding, heavy press-fits, one-way snap or lock features, pressed pins, heat staking, and rivets. Examples of semi-permanent attachments or those that require a tool to separate the components include screws, threaded fasteners, snap-rings, and snap-fits. Examples of releasable attachments or those that can be separated by hand without the use of an additional tool include snap-fits, twist lock features, push to release features, squeeze to release features, slide levers, latches, and light press-fits.

Anchors can have various cross-sectional profiles such as circular, oval, rectangular or other polygon shapes. Anchors can also incorporate external lubricious layers, lubricious coatings, or lubricious wrappings to minimize friction. Anchors can also incorporate therapeutic agents tailored for specific biological results. Anchors can also include radiopaque markers or radiopaque intensifiers.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A medical system comprising:
   an implantable medical device;
   an anchor configured to secure the implantable medical device to tissue, the anchor including a barb portion configured to penetrate a vessel wall, and a compression bearing portion; and
   a constraining member disposed over the implantable medical device and configured to bear against the compression bearing portion and separate the barb portion from the constraining member in a compacted state and expand the bearing portion and barb portion to contact a vessel wall upon removal thereof.

2. The system of claim 1, wherein the implantable medical device is operable to transition between expanded and constrained states, and wherein the compression bearing portion effects separation between the constraining member and the barb when the implantable medical device is in the constrained state.

3. The system of claim 2, wherein anchor further includes an attachment portion, and wherein in the constrained state the barb portion and the attachment portion are aligned with one another.

4. The system of claim 2, wherein in the constrained state the constraining member is operable to maintain a separation between the vessel wall and the barb portion, and wherein in the expanded state the barb portion is operable to penetrate the vessel wall.

5. The system of claim 3, wherein the anchor is configured such that the barb portion is operable to deflect radially outwardly from the implantable medical device when the compression bearing portion is disengaged from the constraining member.

6. The system of claim 2, wherein the compression bearing portion includes an apex, and wherein the constraining member bears against the apex of the compression bearing portion in the constrained state, such that the bearing portion is configured to maintain separation between the vessel wall and the barb portion prior to disengagement of the compression bearing portion from the constraining member.

7. The system of claim 5, wherein the apex of the compression bearing portion protrudes radially outwardly from the implantable medical device in the constrained state.

8. The system of claim 5, wherein the apex of the compression bearing portion protrudes radially outwardly from the barb portion of the anchor in the constrained state.

9. The system of claim 1, wherein the anchor is coupled to the implantable medical device.

10. The system of claim 1, wherein the anchor is integral with the implantable medical device.

11. The system of claim 1, wherein the constraining member is configured to be removed from the implantable medical device by sliding the constraining member relative to the implantable medical device such that the compression bearing portion maintains the separation between the constraining member and the barb as the constraining member slides relative to the implantable medical device.

12. The system of claim 1, wherein the barb portion includes a tip that is configured to penetrate the vessel wall.

13. The system of claim 1, wherein the implantable medical device is a self-expanding medical device.

14. The system of claim 1, wherein the barb portion is configured to self-expand in response to the constraining member being removed from the implantable medical device.

15. A medical system comprising:
an implantable medical device;
an anchor configured to secure the implantable medical device to tissue, the anchor including a barb portion configured to penetrate a vessel wall, a device attachment portion, and a compression bearing portion, a hinge being defined between the compression bearing portion and the device attachment portion; and
a constraining member disposed over the implantable medical device and configured to bear against the compression bearing portion and separate the barb portion is separated from the constraining member in a compacted state and expand the bearing portion and barb portion to contact a vessel wall upon removal thereof.

16. The system of claim 15, wherein the anchor is the compression bearing portion and the barb portion change orientation relative to the device attachment portion when the constraining member is removed from the implantable medical device relative to when the constraining member is disposed over the implantable medical device.

17. The system of claim 15, wherein the compression bearing portion projects radially outwardly of the barb portion to affect the separation between the barb portion and the constraining member.

18. A medical system comprising:
an implantable medical device;
an anchor configured to secure the implantable medical device to tissue, the anchor including a barb portion configured to penetrate a vessel wall, and a compression bearing portion; and
a constraining member disposed over the implantable medical device and configured to engage with the compression bearing portion such that the compression bearing portion projects radially outwardly of the barb portion to affect a separation between the barb portion and the constraining member in a compacted state and expand the bearing portion and barb portion to contact a vessel wall upon removal thereof.

19. The system of claim 18, wherein the compression bearing portion is curved.

20. The system of claim 18, wherein the anchor is configured such that the compression bearing portion projects radially outwardly of the barb portion when constrained by the constraining member, and such that the barb portion projects radially outwardly of the compression bearing portion when the constraining member is removed.

* * * * *